United States Patent [19]
Schultz et al.

[11] Patent Number: 5,730,907
[45] Date of Patent: Mar. 24, 1998

[54] ENHANCED WOOD PRESERVATIVE COMPOSITION

[75] Inventors: Tor P. Schultz; Darrel D. Nicholas, both of Starkville, Miss.

[73] Assignee: Mississippi State University, Mississippi State, Miss.

[21] Appl. No.: 708,126

[22] Filed: Aug. 27, 1996

[51] Int. Cl.$^6$ .................... A01N 43/74; A01N 37/34; A01N 33/04
[52] U.S. Cl. ............... 252/400.62; 252/404; 514/456; 514/642; 514/372; 514/646
[58] Field of Search ................... 564/2; 549/201; 252/400.62, 404; 514/456, 642, 372, 646

[56] References Cited

U.S. PATENT DOCUMENTS

| | | | |
|---|---|---|---|
| 4,400,298 | 8/1983 | Boocock et al. | 252/400 R |
| 4,839,373 | 6/1989 | Ito et al. | 514/367 |
| 4,950,685 | 8/1990 | Ward | 514/479 |
| 5,179,116 | 1/1993 | Goettsche et al. | 514/388 |
| 5,185,214 | 2/1993 | LeVan et al. | 428/541 |
| 5,300,520 | 4/1994 | Igarashi et al. | 514/367 |
| 5,536,305 | 7/1996 | Yu | 106/18.33 |

OTHER PUBLICATIONS

Schultz, et al., Phytochemistry, 29(5), 1501–7 (1990).
Imsgard et al., Rec. Annu. Conv. Br. Wood Preserv. Assoc., 47–54 (1985).

*Primary Examiner*—Johann Richter
*Assistant Examiner*—Laura R. C. Lutz
*Attorney, Agent, or Firm*—Darby & Darby

[57] ABSTRACT

A wood preservative composition comprising a biocide such as a quaternary ammonium compound, e.g., didecyldimethyl ammonium chloride (DDAC), an isothiazolone or an isophthalonitrile, in combination with an antioxidant, which is a flavone or a phenol, is useful as a cost-effective and environmentally safe wood preservative. The invention also provides a method for the use of such composition and compositions so treated.

19 Claims, No Drawings

ENHANCED WOOD PRESERVATIVE COMPOSITION

BACKGROUND OF THE INVENTION

Hardwoods constitute over one-third of the U.S. timber resource. However, with the exception of crossties, hardwoods are rarely treated for exterior use applications, and demand for treated hardwood products has until recently been low. In view of the projected softwood timber shortage and relative abundance of hardwoods, expanded use of treated hardwoods for both composite and solid wood products is expected. The problem is that replacing softwoods with hardwoods is not straightforward since most wood preservatives, including second generation biocides, are considerably less effective when used to treat hardwoods. (Nicholas, D. D., Proc. of the Northern Hardwood Resource: Management and Potential Conference, Heighten, Mich., Aug. 18–20 (1986); Preston, A. F., et al., Proc. Am. Wood Preservers' Assn., 79, 207 (1983)). This disparity is attributable to the considerably higher toxic threshold values obtained when treated hardwoods are attacked by white- and soft-rot fungi as compared to softwoods treated with the same biocide and exposed to brown-rot fungi. (Nicholas, supra). Accordingly, the object of the present invention is to provide wood preservative systems that are effective in protecting hardwoods and providing greater efficacy for softwoods.

An apparent solution to the problem of preserving hardwoods is to use substantially higher biocide levels, but this approach leads to higher costs and increased environmental risks. A more attractive solution would be to increase the efficacy of biocides for treating hardwoods.

In addition, more environmentally benign preservatives to treat softwoods are needed, since all major wood preservatives used today to protect softwoods have perceived environmental problems.

Prior to the present invention, antioxidants have been used in wood treatments of various kinds, but never in conjunction with a biocide to generate a synergistic and environmentally safe preservative for both hardwoods and softwoods. In most previous wood preservatives containing antioxidants, their purpose was merely to stabilize the mixture from chemical decomposition or as a color stabilizer. For example, U.S. Pat. No. 1,168,062 discloses the use of oxidation inhibitors as an additive in oil-in-water emulsions for use in wood preservatives which contain pentachlorophenol as the active ingredient. U.S. Pat. No. 3,889,020 provides di-t-butyl cresol (also called butylated hydroxytoluene, or BHT) as a stabilizer for pentachlorophenol-based preservatives wherein the cresol is intended to improve the surface color of treated poles.

U.K. Patent Application GB 2,025,769A discloses the use of antioxidants, selected from such compound classes as sulfites, hydrosulfides, hydrazines and thiosemicarbazides. The purpose of the antioxidant there is to stabilize biocides from decomposition. U.S. Pat. No. 3,881,940 describes a composition containing an antioxidant stabilizer such as di-t-butylcresol in a biocide comprising a heavy metal oxide and pentachlorophenol. The antioxidant served to prevent discoloration of wood and to prevent sludge formation during treating steps.

U.S. Pat. No. 4,400,298 teaches the combination of dithiocarbamate and a borate with an antioxidant stabilizing agent, e.g., potassium metabisulfite, for the prevention of fungal decay in wood. U.S. Pat. No. 4,783,221 describes wood preservatives containing an isothiazolone and metal salts of carboxylic acids, to which various additives are added including antioxidants. U.S. Pat. No. 5,462,589 discloses a synergistic wood preservative composition comprising copper and organic derivatives, of which antioxidants are recited as possible additives.

Despite these teachings of antioxidants in wood treatment products, usually as stabilizers, synergistic enhancement of biocide effectiveness by antioxidants was unknown prior to the present invention. Moreover, this approach has never before been applied to provide an effective wood preservative for hardwoods.

SUMMARY OF THE INVENTION

The present invention relates to the unexpected utility of adding free radical scavengers (antioxidants) to commercial biocides to protect hardwoods from fungal decomposition. Selected antioxidants significantly increase the activity and effectiveness of biocides to treat hardwoods.

Accordingly, the present invention provides a wood preservative composition comprising (A) at least one biocide selected from the group consisting of a quaternary ammonium compound, an isothiazolone, and an isophthalonitrile and (B) at least one antioxidant. The composition is especially effective when the antioxidant is a flavonoid or a phenol.

In addition to being highly effective, the wood preservative composition is environmentally safe and inexpensive to apply. Of particular practical importance is the discovery that the low-cost antioxidant BHT, which is commonly used as a food additive, when combined with a biocide has an enhanced and synergistic biocidal effect with minimal environmental effects.

DETAILED DESCRIPTION

The present invention provides a wood preservative composition comprising:

A. an effective amount of at least one biocide selected from the group consisting of:

(1) a quaternary ammonium compound having the structure:

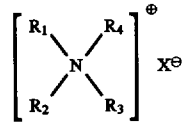

wherein $R_1$ is a $C_{8-12}$ alkyl group or an aralkyl group, or a chloro- or $C_{1-8}$ alkyl-substituted aralkyl group; $R_2$ is a $C_{8-12}$ alkyl group; $R_3$ and $R_4$ are the same or different and are a $C_{1-4}$ alkyl group, a $C_{1-4}$ hydroxyalkyl group, an aralkyl group, or a chloro- or $C_{1-8}$ alkyl-substituted aralkyl group; and X is a halide or an alkylsulfate;

(2) an isothiazolone having the structure:

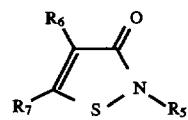

wherein $R_5$ is a substituted or unsubstituted $C_{1-12}$ alkyl, $C_{3-8}$ cycloalkyl, alkenyl, alkynyl, aryl or aralkyl group; and $R_6$ and $R_7$ are the same or different and are hydrogen, a halogen or a substituted or unsubstituted $C_{1-12}$ alkyl, aryl or aralykyl group; and (3) an isophthalonitrile having the structure:

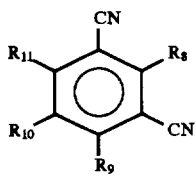

wherein $R_8$, $R_9$, $R_{10}$ and $R_{11}$ are the same or different and are hydrogen, a halogen or a $C_{1-12}$ alkyl group; and B. an effective amount of at least one antioxidant.

The present invention also provides a wood preservative composition as disclosed above wherein the antioxidant is:

(1) a flavonoid having the structure:

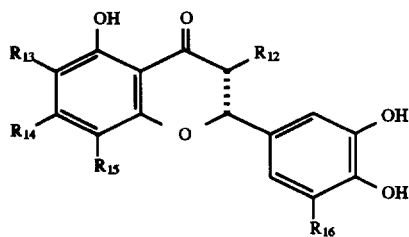

wherein $R_{12}$, $R_{13}$, $R_{14}$, $R_{15}$ and $R_{16}$ are the same or different and are hydrogen, hydroxyl or a $C_{1-12}$ alkoxy group; and wherein the dashed line represents a single or double bond; or (2) a phenol having the structure:

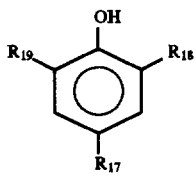

wherein $R_{17}$, $R_{18}$ and $R_{19}$ are the same or different and are hydrogen, halogen, methoxyl, a $C_{2-12}$ alkoxyl or a $C_{1-12}$ alkyl group. Other antioxidants which may be used include dimers, trimers or tetramers of the basic structure above such as tetrakis[methylene(3,5-di-t-butyl-4-hydroxy hydrocinnamate)] or 4,4'-methylenebis(2,6-di-t-butylphenol). Additional antioxidants include, but are not limited to, natural polymeric phenolic materials, such as tannins isolated from the wood or bark of woody plants, and lignins isolated from woody plants such as kraft pulping lignin, organosolve lignin, autohydrolysis lignin, acid-hydrolyzed lignin, steam-exploded lignin and derivatives of isolated lignins. Other classes of antioxidants which are useful include phosphites, phosphonites, thio bisphenols, alkylidene-bisphenols, hydroxybenzyl compounds, acylaminophenols and hydroxyphenylpropionates.

An unsubstituted alkyl group as used in the invention is intended to include straight chain and branched chain alkyl, and when substituted, is meant to encompass an alkyl group having one or more of its hydrogen atoms replaced by another substituent. Examples of the substituted alkyl groups useful in the invention include hydroxyalkyl, haloalkyl, cyanoalkyl, alkylaminoalkyl, dialkylaminoalkyl, arylaminoalkyl, carboxyalkyl, carboalkoxyalkyl, arylthioalkyl, cycloalkylaminoalkyl (e.g., morpholinoalkyl, piperidinoalkyl), alkenyl, haloalkenyl, alkynyl, etc.

A substituted aralkyl group is meant to encompass an aralkyl group having one or more of hydrogen atoms on its aryl ring or alkyl group replaced by another substituent group. A substituted aralkyl group is meant to encompass an aralkyl group having one or more of the hydrogen atoms on its aryl ring or alkyl group replaced by another substituent group. A substituted aryl group is meant to encompass an aryl group having one or more of the hydrogen atoms on its aryl ring replaced by another substituent group.

The quaternary ammonium salt used in the wood preservative composition encompasses compounds wherein $R_1$ and $R_2$ may be the same or different. Examples of $R_1$ and $R_2$ include n-octyl, n-nonyl, n-decyl, n-undecyl and n-do decyl. Examples of $R_3$ include methyl, ethyl, n-propyl, isopropyl, n-butyl, sec-butyl, t-butyl, hydroxyethyl, benzyl, 3-chlorobenzyl, 1,4-dichlorobenzyl, 1,3-dichlorobenzyl, 3-methylbenzyl, 4-methyl, 2,4-dimethylbenzyl, and 3-ethylbenzyl. Examples of $R_4$ include methyl, ethyl, isopropyl, n-propyl, and n-butyl. X may be fluoride, chloride, bromide, iodide, or methylsulfate, ethosulfate. In preferred embodiments, the quaternary ammonium salt is a compound wherein $R_1$ and $R_2$ are bomb n-decyl, $R_3$ and $R_4$ are both methyl, and X is chloride, methosulfate or ethosulfate.

Examples of these quaternary ammonium compounds include didecyldimethylammonium chloride (DDAC), didecyldimethylammonium ethosulfate, didecylmethylpropylammonium bromide, didecylmethylbutylammonium chloride, benzylhexadecyldimethylammonium chloride, didecylmethyl-4-chlorobenzylammonium chloride, didecylmethyl-3,4-dichlorobenzylammonium chloride; decyloctyldimethylammonium chloride, decyloctylbenzylmethylammonium chloride, decyldodecyldimethylammonium chloride, decyldodecylethylmethylammonium chloride, dodecylbenzyldimethylammonium chloride, tetradecylbenzyldimethylammonium chloride, diundecyldimethylammonium chloride, dinonylhydroxyethylmethylammonium chloride, didecylhydroxypropylmethylammonium chloride, and diundecyldihydroxyethylammonium chloride. Blends of compounds containing dioctyl, didodecyl and decyloctyl compounds or didecyl, didodecyl and decyldodecyl compounds may also be used. In addition, mixtures of $C_{12}$,$C_{14}$ and/or $C_{16}$ alkyldodecylbenzylammonium chlorides are useful in practising the invention.

Examples of the substituted alkyl groups characteristic of 3-isothiazolones useful in the invention include hydroxymethyl, hydroxyethyl, methoxymethyl, ethoxymethyl, ethyoxyethyl, aminoethyl, N-acetylaminomethyl, N-acetylaminoethyl, carboxy, methoxycarbonyl, ethoxycarbonyl, trifluoromethyl, trifluoroethyl, pentafluoroethyl, etc.

Examples of the substituted aralkyl groups characteristic of 3-isothiazolones useful in the invention include halogen-, lower alkyl- and lower alkoxy-aralkyl groups. Examples of substituents for aryl groups in 3-isothiazolones useful in practising the invention include halogen, nitro, lower alkyl, lower alkyl-acylamino, lower carbalkoxy, sulfamyl, etc.

Specific 3-isothiazolones used as a biocide in the composition include compounds wherein $R_5$ is n-octyl, and $R_6$ and $R_7$ are both chloride; wherein $R_5$ is n-decyl, and $R_6$ and $R_7$ are both chloride; wherein $R_5$ is n-octyl, and $R_6$ is hydrogen and $R_7$ is chloride; and wherein $R_5$ is n-octyl, and $R_6$ is chloride and $R_7$ is phenyl.

The halogen in the isophthalonitrile used as a biocide in the composition may be fluoride, bromide, chloride or iodide. Preferably, the halogen is chloride. The alkyl group in the isophthalonitrile may be unsubstituted or substituted as described below.

Specific isophthalonitriles useful in the invention include compounds having the above-shown structure wherein $R_8$, $R_9$, $R_{10}$ and $R_{11}$ are all chloride (chlorothalonil); wherein $R_8$ and $R_9$ are hydrogen and $R_{10}$ and $R_{11}$ are both chloride; wherein $R_8$ and $R_{11}$ are both hydrogen and $R_9$ is methyl and $R_{10}$ are chloride; wherein $R_9$ and $R_{11}$ are both hydrogen and $R_8$ and $R_{10}$ are both chloride.

Specific examples of phenols used as antioxidants in the invention include the phenol shown above wherein $R_{17}$ is methoxyl or methyl and $R_{18}$ and $R_{19}$ are both t-butyl (butylated hydroxy toluene (BHT)or butylated hydroxy anisole (BHA)); and the phenol wherein $R_{17}$ is hydrogen and $R_{18}$ and $R_{19}$ are both t-butyl. Preferably, $R_{18}$ and $R_{19}$ are t-butyl.

The flavonoid used as an antioxidant includes compounds wherein $R_{12}$ and $R_{14}$ are both hydroxyl and $R_{13}$, $R_{15}$ and $R_{16}$ are all hydrogen, and wherein the dashed line signifies a double bond (quercetin); the flavonoid wherein $R_{12}$ and $R_{14}$ are both hydroxyl and $R_{13}$, $R_{15}$ and $R_{16}$ are all hydrogen, and wherein the dashed line signifies a double bond. Examples of such flavonoids are, chrysin, luteolin, myrcetin, hespertin and rhamnetin.

The wood preservative composition disclosed herein may further comprise a liquid carrier medium selected from the group consisting of a solvent and a suspending agent. Preferably, the liquid carrier medium is a solvent such as methanol, ethanol, alcohols, water, ethyl acetate, toluene, a paraffinic hydrocarbon or di chloromethane. The suspending agent may be a foam or gel. The composition may also be applied as a solution in miscible mixtures of solvents or as an emulsion in multiphasic media. If desired, buffers, water-repellents, insecticides, pigments, odorants, coloring agents, surfactants, flame-retardant compositions and other additives may be added to the treating solution. The amount of such additives may vary over a range from about 0.01% to about 7%. The composition of the invention may be provided not only as a diluted solution but also as a concentrate comprising an undiluted solution, emulsion or suspension of biocide and antioxidant which may be diluted with any of the above-named solvents. The composition may also be formulated without added solvent or diluent as a powder or pellets.

The amount of the biocidal composition used in the composition and method of the invention is a "biocidal effective amount," i.e., an amount effective to inhibit the growth of, or kill, one or more organisms that cause wood rot. Such organisms include but are not limited to P. placenta, T. versicolor, Irpex lacteus (I. lacteus) and Gloeophyllum trabeum (G. trabeum). In the wood preservative composition of the invention, the weight ratio of the biocide to the antioxidant is from about 0.10:1 to about 3:1, preferably from about 0.50:1 to about 2:1. The biocide may be present in an amount of from about 0.01 to about 10% by weight and the antioxidant in an amount of from about 0.10 to about 12% by weight.

In pressure-treating wood with the present compositions, roughly 1 gallon of treating solution is used for each board-foot of lumber with about 20% to about 50% of the solution being absorbed by the wood. Contact times of about 2 hours are typically used. Generally, 1,000 board feet of lumber require about 1,000 gallons of treating solution which is administered during a contact period of between about 1 and about 6 hours.

The present invention also provides a method for preserving wood against destructive fungi which comprises contacting wood with a biocidally effective concentration of the wood preservative composition as defined above in a carrier liquid. Accordingly, the method permits preserving wood against at least one fungus selected from the group consisting of P. placenta, I. lacteus, T. versicolor and G. trabeum.

The components of the present invention are mixed by conventional means known in the art to form an emulsion, such as oil in water microemulsions, or they may alternatively be prepared as solutions. Conventional additives, such as stabilizers, odorants, surfactants, coloring agents, emulsifiers and water repellents, may be added as required for particular applications. Typical amounts of such additives vary from about 0.001% to about 5% by weight.

Treatment of wood, e.g. lumber, timber, etc., can be carried out by conventional techniques including, but not limited to, dipping, spraying, brushing, pressure impregnation, and vacuum treatment. The length of the treatment time required will vary according to the treatment conditions, the selection of which are well known to those skilled in the art.

Throughout this application, various references are cited within parentheses. These publications are hereby incorporated by reference to more fully describe the state of the art to which this invention pertains.

This invention will be better understood from the Examples which follow. However, one skilled in the art will readily appreciate that the specific methods and results discussed are merely illustrative of the invention as described more fully in the claims which follow thereafter. Unless otherwise indicated, all parts and percentages in the Examples and the present specification are by weight.

EXAMPLE 1

Sweetgum sapwood blocks were treated with either didecyldimethylammonium chloride (DOAC) or 4,5-dichloro-2-n-octyl-4-isothiazolin-3-one (Kathon 930™,Rohm & Haas), with and without the antioxidant BHT (Table 1). These blocks were exposed to the white-rot fungus Irpex lacteus for eight weeks in the agar block test described by Archer, K., et al., For. Prod. J., 45(1), 86–89(1995). The average retentions are reported in pounds of preservative per cubic foot of wood (pcf), as is normal in the wood preservative industry. The biocide effectiveness is determined by % weight loss. Average % weight loss was determined for 5 mm×14 mm×14 mm sweetgum sapwood samples using the agar-block test. The wood was exposed to the white-rot fungus I. lacteus for eight weeks, with five replicates per treatment. Methanol was used as the solvent. Five replicates and one untreated (control) sample were run in each agar cup. The results, presented in Table 1, clearly show that the addition of small amounts of BHT produced a substantial increase in the activity of both biocides. For example, adding as little as 0.03 pcf BHT reduced the toxic threshold values of both DDAC and Kathon 930 by over four-fold. This experiment supports the concept that the activity of biocides used as hardwood preservatives can be significantly increased by adding antioxidants.

TABLE 1

Summary of average % weight loss for 5 mm × 14 mm × 14 mm sweetgum sapwood samples using the agar-block test.

| Biocide/Average Retention (pcf) | Avg % Weight Loss ± Std.Dev. |
| --- | --- |
| BHT/0.11 | 22.6 ± 8.7 |
| BHT/0.23 | 23.6 ± 5.9 |
| BHT/0.47 | 20.8 ± 7.1 |
| BHT/0.75 | 24.2 ± 5.4 |
| DDAC/0.03 | 22.8 ± 4.0 |
| DDAC/0.05 | 21.4 ± 2.1 |
| DDAC/0.17 | 15.7 ± 3.1 |
| DDAC/0.29 | 0.10 ± 1.1 |

TABLE 1-continued

Summary of average % weight loss for 5 mm × 14 mm × 14 mm sweetgum sapwood samples using the agar-block test.

| Biocide/Average Retention (pcf) | Avg % Weight Loss ± Std.Dev. |
|---|---|
| BHT/0.03; DDAC/0.03 | 0.8 ± 0.1 |
| BHT/0.05; DDAC/0.05 | 0.8 ± 0.0 |
| BHT/0.17; DDAC/0.17 | 0.9 ± 0.1 |
| BHT/0.20; DDAC/0.20 | 1.0 ± 0.0 |
| BHT/0.19; DDAC/0.10 | 0.8 ± 0.1 |
| Kathon 930/0.02 | 15.4 ± 3.0 |
| Kathon 930/0.03 | 15.9 ± 6.4 |
| Kathon 930/0.07 | 8.3 ± 4.1 |
| Kathon 930/0.12 | 3.0 ± 1.8 |
| Kathon 930/0.17 | −0.4 ± 0.3 |
| BHT/0.03; Kathon 930/0.03 | 0.9 ± 0.0 |
| BHT/0.04; Kathon 930/0.04 | 0.9 ± 0.0 |
| BHT/0.10; Kathon 930/0.05 | 0.9 ± 0.1 |
| BHT/0.17; Kathon 930/0.09 | 1.0 ± 0.0 |
| Controls | 22.9 ± 7.6 |

EXAMPLE 2

To show that free radical scavengers (primary antioxidants) will increase the efficacy of commercial biocides used as wood preservatives, two tests are performed: (1) soil-block and/or agar-block tests and (2) unsterile soft-rot test.

Three commercial biocides were selected for the soil block experiments: DDAC (didecyldimethylammonium chloride), chlorothalonil (2,4,5,6-tetrachloroisophthalonitrile), and Kathon 930 (4,5-dichloro-2-n-octyl-4-isothiazolin-3-one). These three biocides show promise as potential wood preservatives (Nicholas, D. D. and T. P. Schultz, "Biocides That Have Potential as Wood Preservative—An Overview," *Forest Prod. Soc. Proc., Wood Preservation in the '90s and Beyond* (1995)), and are either hydrophilic (DDAC) or hydrophobic. The antioxidants used include the commercial hydrophobic antioxidant BHT and the natural hydrophilic antioxidant quercetin.

The agar plate method was used (Behr, "Decay Test Methods," *Wood Deterioration and Its Prevention by Preservation Treatments I*, D. Nicholas, ed., Syracuse Univ. Press (1973)). In this method agar nutrient solutions with various concentrations of biocides are prepared. A plug of agar with actively growing fungus is placed in the center of each plate and the relative mycelium growth for the treated agar is compared to the untreated (control) agar plate. The plates are placed in an incubator at 28° C. The minimal concentration of biocide composition which totally inhibits fungal growth (MIC) and the concentration at which the mycelium radial growth is inhibited by 50% ($IC_{50}$) can then be calculated.

The wood used in the agar- or soil-block tests includes sweetgum sapwood and southern pine sapwood, selected according to AWPA standard E 10-91. The white-rot fungi examined were *T. versicolor* (ATCC#12679) and *I. lacteus* (ATCC#11245) and the brown-rotters were *G. trabeum* (ATCC#11539) and *P. placenta* (ATCC#11538). Samples treated with the biocide alone at five different retention levels were directly compared with similar samples treated with the biocide at the same retention levels plus one of the two antioxidants at a single retention level. Untreated samples and samples treated only with the antioxidants served as controls.

There is currently no standard method for evaluating wood preservatives against soft-rot fungi, so the soil bed method developed by Nicholas, D. D., et al., *Effect of Soft-rot Decay on the Static Bending Strength of Wood, Intern. Res. Gp. on Wood Pres.*, Doc. No. IRG/WP/2361 (1991)) was used. In this method, thin (3 mm×19 mm×250 mm; t×r×l) sticks are exposed to unsterile soil maintained at a moisture content sufficiently high to favor soft-rot fungi. The degree of soft-rot attack is determined by periodically measuring the bending stiffness of each specimen. The soft-rot tests were carried out with sweetgum sapwood samples treated with the combinations of biocides and antioxidants shown in Table 2. This soil bed was maintained at a moisture content level that provides a minimum equilibrium moisture content of approximately 60% in the test samples. The test samples were removed and evaluated for bending stiffness approximately every 60 days.

TABLE 2

Treatments for Soft-rot and Soil-block Tests.

| Components | Treating Solution Biocide/Additive Conc. (% a.i.) |
|---|---|
| DDAC | 0.20, 0.50, 0.75, 1.00, 1.50 |
| DDAC/BHT | 0.20/0.50, 0.50/0.50/0.75/0.50, 1.00/0.50, 1.50/0.50 |
| DDAC/Quercetin | 0.20/0.50, 0.50/0.50/0.75/0.50, 1.00/0.50, 1.50/0.50 |
| Chlorothalonil | 0.20, 0.40, 0.60, 1.00 |
| Chlorothalonil/BHT | 0.20/0.50, 0.40/0.50, 0.60/0.50, 1.00/0.50 |
| Chlorothalonil/Quercetin | 0.20/0.50, 0.40/0.50, 0.60/0.50, 1.00/0.50 |
| Kathon 930 | 0.05/0.50, 0.10/0.50, 0.20/0.50, 0.50/0.50 |
| Kathon 930/BHT | 0.05/0.50, 0.10/0.50, 0.20/0.50, 0.50/0.50 |
| Kathon 930/Quercetin | 0.05/0.50, 0.10/0.50, 0.20/0.50, 0.50/0.50 |

DISCUSSION

These tests show that the efficacy of biocides to protect hardwoods can be significantly enhanced by the method disclosed herein. Specifically, the addition of an antioxidant to biocides results in a significantly more active wood preservative.

The present inventors have determined that the preservative system disclosed herein can be used for both composite products that utilize hardwoods and softwoods as well as solid wood products and, as a result, greatly increase the utilization of hardwoods in applications where the product is susceptible to biodeterioration. Composite products are of particular interest because most of them contain hardwoods. However, for ecological and economic reasons, it is desirable to minimize the amount of biocide used to achieve a preservative effect. Accordingly, the addition of antioxidants in accord with the present invention should reduce the preservative retention levels required, and consequently, greatly improve the economics of both hardwood and softwood preservative systems, and thereby provide a more environmentally benign approach to the preservation of wood.

Variations of the present invention will suggest themselves to those skilled in the art, and are within the scope of the following claims.

What is claimed is:

1. A wood preservative composition comprising:
   (1) an effective mount of at least one biocide selected from the group consisting of:
      (a) a quaternary ammonium compound having the structure:

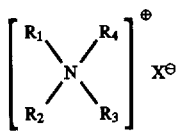

wherein $R_1$ is a $C_{8-12}$ alkyl group or an aralkyl group, or a chloro- or $C_{1-8}$ alkyl-substituted aralkyl group; $R_2$ is a $C_{8-12}$ alkyl group; $R_3$ and $R_4$ are the same or different and are a $C_{1-4}$ alkyl group, a $C_{1-4}$ hydroxyalkyl group, an aralkyl group, or a chloro- or $C_{1-8}$ alkyl-substituted aralkyl group; and X is a halide or an alkylsulfate;

(b) an isothiazolone having the structure:

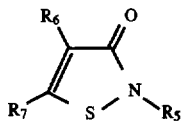

wherein $R_5$ is a substituted or unsubstituted $C_{1-12}$ alkyl, aryl or aralkyl group; and $R_6$ and $R_7$ are the same or different and are hydrogen, a halogen or a substituted or unsubstituted $C_{1-12}$ alkyl, aryl or aralykyl group;

(c) an isophthalonitrile having the structure:

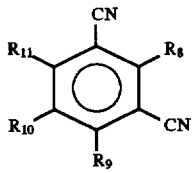

wherein $R_8$, $R_9$, $R_{10}$ and $R_{11}$ are the same or different and are hydrogen, a halogen or a $C_{1-12}$ alkyl group, wherein when an isothiazolone is selected, then a quaternary ammonium compound or an isophthalonitrile is also selected; and (2) an effective amount of at least one antioxidant selected from the group consisting of:
(a) a flavonoid having the structure:

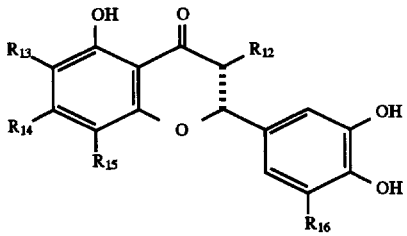

wherein $R_{12}$, $R_{13}$, $R_{14}$, $R_{15}$ and $R_{16}$ are the same or different and are hydrogen, hydroxyl or a $C_{1-12}$ alkoxy group; and wherein the dashed line represents a single or double bond; or
(b) a phenol having the structure:

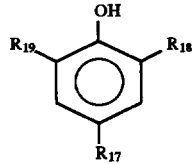

wherein $R_{17}$, $R_{18}$ and $R_{19}$ are the same or different and are hydrogen, halogen, methoxyl, a $C_{2-12}$ alkoxyl or a $C_{1-12}$ alkyl group.

2. The wood preservative composition of claim 1 wherein the biocide is the quaternary ammonium salt wherein $R_1$ and $R_2$ are n-decyl, and $R_3$ and $R_4$ are methyl.

3. The wood preservative composition of claim 2 wherein X in the quaternary ammonium salt is chloride, methosulfate or ethosulfate.

4. The wood preservative composition of claim 2 wherein the antioxidant is the phenol wherein $R_{17}$ is methyl and $R_{18}$ and $R_{19}$ are t-butyl; or the flavonoid wherein $R_{12}$ and $R_{14}$ are hydroxyl and $R_{13}$, $R_{15}$ and $R_{16}$ are hydrogen, and wherein the dashed line signifies a double bond.

5. The wood preservative composition of claim 1 wherein the biocide is the isothiazolin-3-one wherein $R_5$ is n-octyl, and $R_6$ and $R_7$ are chloride.

6. The wood preservative composition of claim 5 wherein the antioxidant is the phenol wherein $R_{17}$ is methyl and $R_{18}$ and $R_{19}$ are t-butyl; or the flavonoid wherein $R_{12}$ and $R_{14}$ are hydroxyl and $R_{13}$; $R_{15}$ and $R_{16}$ are hydrogen, and wherein the dashed line signifies a double bond.

7. The wood preservative composition of claim 1 wherein the biocide is the isophthalonitrile wherein $R_8$, $R_9$, $R_{10}$ and $R_{11}$ are chloride.

8. The wood preservative composition of claim 7 wherein the antioxidant is the phenol wherein $R_{17}$ is methyl and $R_{18}$ and $R_{19}$ are t-butyl; or the flavonoid wherein $R_{12}$ and $R_{14}$ are hydroxyl and $R_{13}$, $R_{15}$ and $R_{16}$ are hydrogen, and wherein the dashed line signifies a double bond.

9. The wood preservative composition of claim 1 further comprising a liquid carrier medium selected from the group consisting of a solvent or suspending agent.

10. The wood preservative composition of claim 9 wherein the liquid carrier medium is selected from the group consisting of methanol, ethanol, water, ethyl acetate, and dichloromethane.

11. The wood preservative composition of claim 1 wherein the weight ratio of at least one biocide to at least one antioxidant is from about 0.10:1 to about 3:1.

12. The wood preservative composition of claim 11 wherein the weight ratio is from about 0.50:1 to about 2:1.

13. The wood preservative composition of claim 1 wherein the biocide is present in an amount of from about 0.01 to about 10% by weight and the antioxidant is present in an amount of from about 0.10 to about 12% by weight.

14. The wood preservative composition of claim 13 wherein the antioxidant is the phenol wherein $R_{17}$ is methyl and $R_{18}$ and $R_{19}$ are t-butyl; or the flavonoid wherein $R_{12}$ and $R_{14}$ are hydroxyl and $R_{13}$, $R_{15}$ and $R_{16}$ are hydrogen, and wherein the dashed line signifies a double bond.

15. The wood preservative composition of claim 13 wherein the biocide is the isophthalonitrile wherein $R_8$, $R_9$, $R_{10}$ and $R_{11}$ are chloride; the quaternary ammonium salt wherein $R_1$ and $R_2$ are n-decyl, $R_3$ and $R_4$ are methyl and X is chloride; or the isothiazolin-3-one wherein $R_5$ is n-octyl, and $R_6$ and $R_7$ are chloride.

16. A method of preserving wood which comprises contacting wood with the wood preservative composition of claim 1.

17. A method of preserving wood which comprises contacting wood with the wood preservative composition of claim 13.

18. The method of preserving wood of claim 17 wherein the antioxidant is the phenol wherein $R_{17}$ is methyl and $R_{18}$ and $R_{19}$ are t-butyl; or the flavonoid wherein $R_{12}$ and $R_{14}$ are hydroxyl and $R_{13}$, $R_{15}$ and $R_{16}$ are hydrogen, and wherein the dashed line signifies a double bond.

19. The method of preserving wood of claim 17 wherein the biocide is the isophthalonitrile wherein $R_8$, $R_9$, $R_{10}$ and $R_{11}$ are chloride; the quaternary ammonium salt wherein $R_1$ and $R_2$ are n-decyl, $R_3$ and $R_4$ are methyl and X is chloride; or the isothiazolin-3-one wherein $R_5$ is n-octyl, and $R_6$ and $R_7$ are chloride.

* * * * *